US00PP12279P2

(12) United States Plant Patent
Stemkens

(10) Patent No.: US PP12,279 P2
(45) Date of Patent: Dec. 11, 2001

(54) VERBENA PLANT NAMED 'VILENA'

(75) Inventor: Henricus G. W. Stemkens, Hoorn (NL)

(73) Assignee: Syngenta Seeds B.V., Enkhuisen (NL)

( * ) Notice: Subject to any disclaimer, the term of this patent is extended or adjusted under 35 U.S.C. 154(b) by 0 days.

(21) Appl. No.: 09/615,040

(22) Filed: Jul. 13, 2000

(51) Int. Cl.[7] ..... A01H 5/00
(52) U.S. Cl. ..... Plt./308
(58) Field of Search ..... Plt./308

(56) References Cited

U.S. PATENT DOCUMENTS

P.P. 11,791 * 2/2001 Perkins ..... Plt./308

OTHER PUBLICATIONS

UPOV–ROM GTITM Computer Database 2001/02, Apr. 2, 2001, GTI Jouve Retrieval Software, Citation for Verbena 'Vilena'.*

* cited by examiner

*Primary Examiner*—Bruce R. Campell
*Assistant Examiner*—June Hwu
(74) *Attorney, Agent, or Firm*—Bruce Vrana

(57) ABSTRACT

A new Verbena plant particularly distinguished by its violet blue flower, early flowering, feathered leaves, and spreading habit that becomes hanging as plant develops.

1 Drawing Sheet

BACKGROUND OF THE NEW PLANT

The present invention comprises a new distinct cultivar of Verbena, botanically known as *Verbena×hybrida*. The new cultivar is propagated from cuttings resulting from the cross of 'W701' and 'W723'. 'W701' is a purple flowering Verbena having a spreading habit. 'W701' is not commercially available and is not known by any synonyms. 'W723' is a pink flowering Verbena having a spreading habit. 'W723' is not commercially available and is not known by any synonyms. Neither 'W701' or 'W723' has been patented. As a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Verbena plant is an annual in most climatical zones in the US, only in zones 8, 9 and 10 it is a perennial plant.

DESCRIPTION OF THE DRAWING

This new Verbena plant is illustrated by the accompanying photographic drawings which show blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Verbena. The data which defines these characteristics were collected from asexual reproductions carried out in Enkhuizen, Netherlands. The plant history was taken on 14 weeks old plants, blossomed under natural light in a greenhouse. Color readings were taken in the greenhouse under ambient light. Color references are primarily to the R.H.S. Color Chart of The Royal Horticultural Society of London.

Differences between the new variety 'Vilena', its parents and a similar cultivar

| | Character | | | |
|---|---|---|---|---|
| | 'Vilena' | 'W711' | 'W681' | 'Tapien violet' |
| Flower Color | light violet blue | purple | pink | violet blue |
| Seed set | no | no | yes | no |
| Earliness | early | late | very early | very late |

THE PLANT

Classification — Botanical: *Verbena×hybrida.*
Parentage:
*Female parent.*—A seedling named 'W701' is one of our seedlings from our W-generation of plants bred in 1992.
*Pollen parent.*—A seedling named 'W723' is one of our seedlings from our W-generation of plants bred in 1992.
Growth habit: Spreading and hanging.
Plant height: 12–20 cm.
Spreading area of plant: 50–90 cm.
Growth rate: Vigorous.
Strength: Very good.
Branching character: Freely branching and lateral branching at every node.
Blooming period: From April until November.

The Stem

Diameter: 1–2 mm.
Shape: Tetragonal.
Anthocyan pigmentation: Absent.

Length of internode: 15–30 mm, depending on the light where the plant is propagated.
Pubescence: Slightly pubescent.

The Foliage

Phyllotaxis: Opposite.
Shape of blade: Broadly ovate, pinnatisect.
Texture:
*Upper side.*—Smooth.
*Lower side.*—Smooth.
Venation: Pinnate.
Leaf margin: Double incised.
Leaf base: Truncate.
Leaf apex: Acuminate.
Length: 20–40 mm.
Width: 22–44 mm.
Depth of incision: 10–25 mm.
Color:
*Upper side.*—Dark green 137A.
*Lower side.*—Light green 138A.
Pubescence: Some pubescence is present.
Length of leaf stem: 5–10 mm.
Petiole surface structure: Slightly pubescent.

The Bud

Peduncle length: 40–70 mm, depending on season.
Size:
*Diameter.*—2 mm.
*Length.*—8–12 mm.
Shape: Elongated and ovate.
Color: Medium green 137C.
Sepals:
*Color.*—Light green 138A.
*Form.*—Upright.
*Number.*—5, fused.
*Size.*—6 mm.
*Shape.*—Elongated.

The Flower

Direction: Ascending.
Diameter: 14–16 mm.
Height: 16–18 mm.
Borne: In a cluster.
Form: Salverform; sessile on terminal spikes.
Cluster: Spike.
Color: Violet blue 90A, more red towards centre. Older flowers bleach towards Lavender blue 90D.
Eye: A very small (2 mm) Lavender Eye (color: 91A) is present at the base of all petals.
Overlapping of petals: Separate.
No. of petals: Gamapetalous, 5 lobed.
Shape of the petals: Each petal is heart shaped at the apex and grown together at the base.
Size of the petal:
*Length.*—5–7 mm.
*Width.*—4–6 mm.
Spike:
*Length.*—40–70 mm.
*Diameter.*—28–38 mm.
Calyx: Length of 8–10 mm.
Calyx color: 141D.
Calyx surface texture: Smooth.
Anthocyan pigmentation of Calyx limb: Absent.
No. of flowers per spike: 30–50.
Fragrance: A very soft rosy-sweet fragrance.
Lastingness of the bloom: New florets continue to open in one spike over a period of 18 days.
Reproductive organs: One pistil and four stamens in pairs; color for both is yellow green 150C. The pistil size is 14–16 mm in length. Pollen is not present. The filaments and anthers are fused to the corolla. The anthers are enclosed and not prominent feature of the flower. 'Vilena' does not freely set seed.
Roots:
*Type of roots.*—Fibrous. Roots start to grow on every part of the stem that contacts the soil, so not only at the nodes.
Physiological and ecological characteristics: Good tolerance to heat and cold. Strong resistance to pests and diseases, particularly powdery mildew.

What is claimed is:

1. A new and distinct variety of Verbena plant, substantially as herein illustrated and described, characterized particularly as to novelty by violet blue flowers, which appear earlier on the plant, feathered foliage and a growing habit that is first spreading but later hanging.

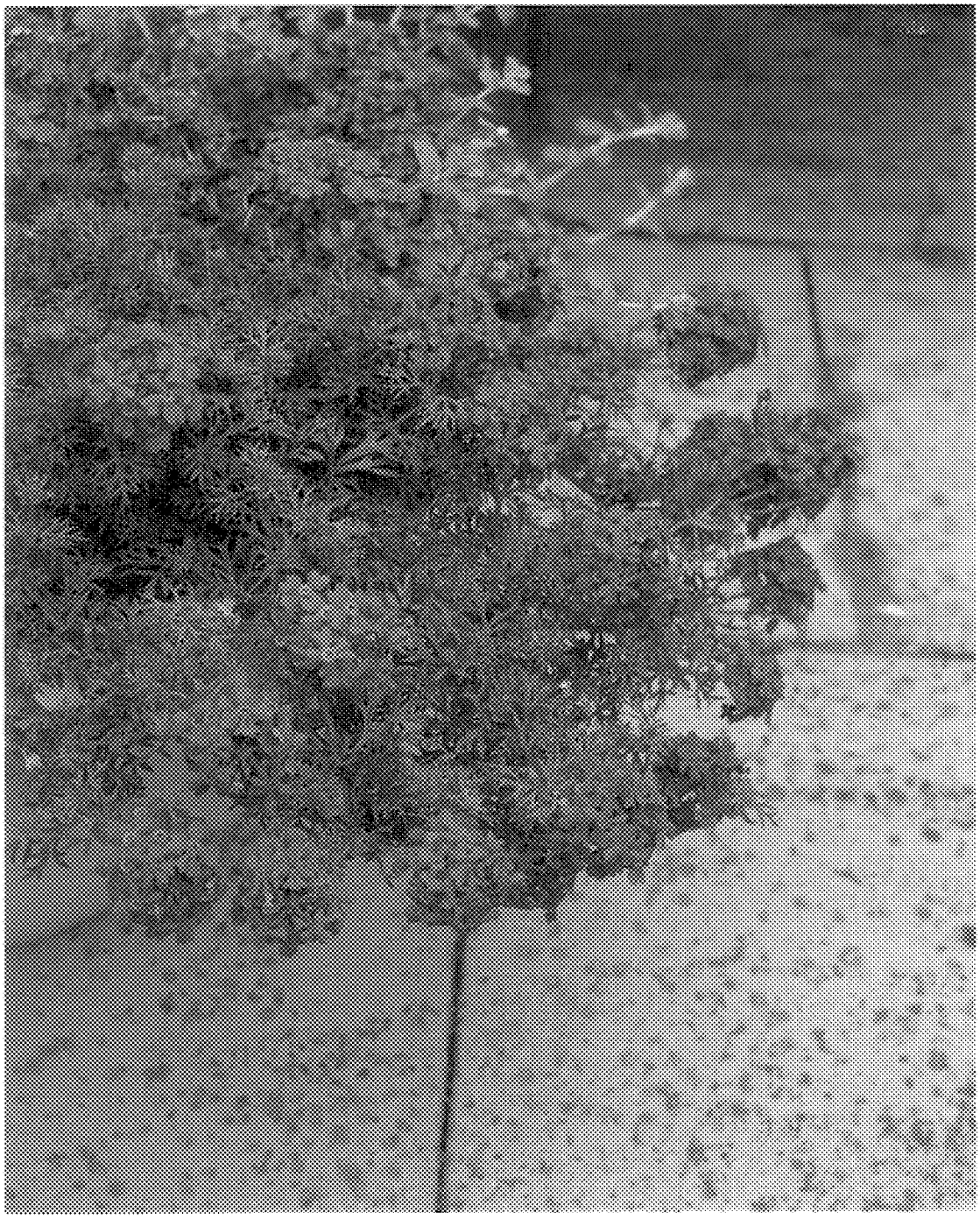

* * * * *